United States Patent [19]

Bliesener et al.

[11] Patent Number: 4,671,816
[45] Date of Patent: Jun. 9, 1987

[54] ACETYLENE COMPOUNDS, THEIR PREPARATION AND THEIR USE FOR REGULATING PLANT GROWTH

[75] Inventors: Jens-Uwe Bliesener, Deidesheim; Manfred Baumann, Mannheim; Werner Hoffmann, Neuhofen; Hubert Sauter, Mannheim; Johann Jung, Limburgerhof, all of Fed. Rep. of Germany

[73] Assignee: BASF Aktiengesellschaft, Ludwigshafen, Fed. Rep. of Germany

[21] Appl. No.: 768,188

[22] Filed: Aug. 23, 1985

Related U.S. Application Data

[63] Continuation of Ser. No. 437,576, Oct. 29, 1982, abandoned.

[51] Int. Cl.$^4$ .................... A01N 43/00; C07D 317/14
[52] U.S. Cl. .......................... 71/88; 549/453; 549/374; 549/347; 549/341; 549/333; 71/122
[58] Field of Search ............... 549/453, 341, 333, 347, 549/374; 71/122, 88

[56] References Cited

U.S. PATENT DOCUMENTS

| 2,802,878 | 8/1957 | Monroe et al. ..................... 71/122 |
| 3,153,097 | 10/1964 | Cameron ............................ 71/122 |
| 3,535,386 | 10/1970 | Dillard .............................. 71/122 |
| 3,576,880 | 4/1971 | Weedon et al. .................... 549/333 |
| 3,946,078 | 3/1976 | Rautenstrauch et al. .......... 568/824 |
| 4,156,090 | 5/1979 | Kienzle ............................. 560/61 |
| 4,227,022 | 10/1980 | Rosenberger ..................... 568/824 |
| 4,233,464 | 11/1980 | Baumann et al. ................. 568/824 |
| 4,324,729 | 4/1982 | Frankhauser ..................... 568/824 |

OTHER PUBLICATIONS

Chem. Abstr. 92, 577 (Nr. 214940e) (1980).

*Primary Examiner*—Nicky Chan
*Attorney, Agent, or Firm*—Keil & Weinkauf

[57] ABSTRACT

Acetylene compounds of the formula

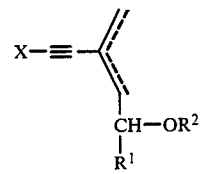

where $R^1$, $R^2$ and X have the meanings given in the description, a process for their preparation and their use for regulating plant growth.

7 Claims, No Drawings

ACETYLENE COMPOUNDS, THEIR PREPARATION AND THEIR USE FOR REGULATING PLANT GROWTH

This application is a continuation of application Ser. No. 437,576, filed on Oct. 29, 1982, now abandoned.

The present invention relates to acetylene compounds, a process for their preparation, plant growth-regulating agents containing these compounds, and their use for regulating plant growth.

It has been disclosed that the phytohormone abscissic acid (ABA) which occurs naturally in plants acts as a regulator in various physiological processes in the plant (Die Pharmazie 27 (1972), 619; B. V. Milborrow "Abscissic Acid" in "Phytohormones and Related Compounds—A Comprehensive Treatise", vol. I, pages 295 et seq., Editors: Letham Goodwin and Higgins, Elsevier 1978).

Thus, ABA influences, for example, the dormancy of seeds and of buds, the ripening of fruit and the abscission process of fruits and leaves, and is particularly important in regulating the water balance in plants. Thus, for example under dry conditions, the endogenic concentration of ABA in the leaves is increased as a result of increased biosynthesis, and this in turn causes the stomata in the leaves to close, with the result that the plant releases less water via the stomata (reduced stomatic transpiration). In this manner, the plant is able to compensate for an inadequate water supply. However, under severe conditions, the action of the endogenic ABA is not always adequate to protect the plant from damage by heat or dryness.

ABA supplied exogenically, for example by spraying the plant with a solution of ABA, causes more extensive closing of the stomata and hence leads to substantially reduced transpiration. As a result, the treated plants are substantially more resistant to the effects of heat and dryness than the untreated ones.

Accordingly, treatment of crop plants with transpiration inhibitors would be very useful in agriculture in practice. Damage to crop plants by heat and dryness is a great problem in arid regions regularly affected by heat or drought. In these regions, there is an urgent need for agents which reduce transpiration in crop plants.

Although exogenically applied ABA, as a result of its biological action, is a suitable transpiration inhibitor for crop plants, it has not been used hitherto in agriculture. The reason for this is that the technical effort required to provide sufficient amounts of ABA is not acceptable with regard to the particular agricultural objective. ABA occurs in plants only in very small amounts, and its isolation from this source involves very substantial expense. On the other hand, the conventional total syntheses of abscisic acid [cf., for example: J. W. Vornforth et al., J. Chem. Soc. C, 1968, 1,565; D. L. Roberts et al., J. Org. Chem., 33 (1968), 3,566; T. Oritani et al., Agric. Biol. Chem. (Tokyo), 34 (1970), 108; J. A. Findlay et al., Can. J. Chem., 49 (1971), 2,369; H. J. Mayer et al., Helv. Chim. Acta, 59 (1976), 1,424; and F. Kienzle et al., Helv. Chim. Acta, 61 (1978), 2,616] are so difficult and expensive, and require so great a technical effort, that they are unsuitable for the preparation of plant growth regulators, in particular of agents for regulating transpiration in crop plants.

We have found that acetylene compounds of the formula

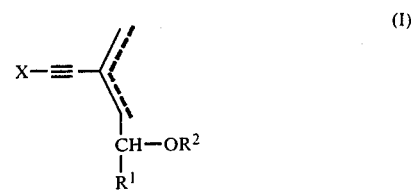

where one of the broken lines is the double bond in each case, $R^1$ is hydrogen or $-OR^2$ and $R^2$ is alkyl of 1 to 6 carbon atoms, or $R^1$ is $-OR^5$, and $R^5$, together with $R^2$, forms a methylene chain of the formula $-(CH_2)_n-$ where n is 2, 3 or 4, and can be monosubstituted or disubstituted by alkyl of 1 to 4 carbon atoms, and X is one of the radicals

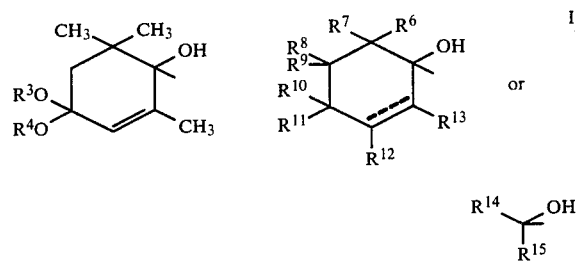

where $R^3$ and $R^4$ are identical and are each alkyl of 1 to 6 carbon atoms, or together form a methylene chain which is of the formula $-(CH_2)_n-$ where n is 2, 3 or 4, and can be monosubstituted or disubstituted by alkyl of 1 to 4 carbon atoms, and $R^6$ is hydrogen, methyl, ethyl, isopropyl or tert.-butyl, $R^8$ is hydrogen, straight-chain or branched alkyl or alkenyl of no more than 4 carbon atoms, and $R^7$, $R^9$, $R^{10}$, $R^{11}$, $R^{12}$ and $R^{13}$ are each hydrogen or methyl, and substituents $R^6$ to $R^{13}$ being in any stereochemical arrangement relative to each other and relative to the acetylenic side-chain and the endocyclic broken line may denote a double bond, and $R^{14}$ and $R^{15}$ are, independently of one another, branched or straight-chain alkyl or alkenyl of no more than 6 carbon atoms, cycloalkyl of 3 to 6 carbon atoms, unsubstituted or substituted phenyl or unsubstituted or substituted aralkyl, have a very good plant growth-regulating action, in particular a very good transpiration-inhibiting action, and can be prepared in a relatively simple manner, without excessively great technical effort.

Preferred acetylene compounds of the formula I are those in which $R^1$ is $OR^2$, where $R^2$ is alkyl of 1 to 4 carbon atoms, and furthermore those in which $R^1$ is $-OR^5$, and $R^5$, together with $R^2$, forms a methylene chain which is of the formula $-(CH_2)_n-$ where n is particularly preferably 2, and can be substituted by methyl or ethyl.

Further preferred compounds are those in which $R^3$ and $R^4$ are identical and are each alkyl of 1 to 4 carbon atoms, and those in which $R^3$ and $R^4$ form a methylene chain which is of the formula $-(CH_2)_n-$ where n is particularly preferably 2, and can be substituted by methyl or ethyl.

Furthermore, in formula I, $R^6$ is preferably $CH_3$, $R^7$ is preferably H or $CH_3$, $R^8$ is preferably H or $CH_3$, $R^9$ is preferably H, $R^{10}$, $R^{11}$ and $R^{12}$ are each preferably H, and $R^{13}$ is preferably $CH_3$.

In formula I, suitable radicals $R^{14}$ and $R^{15}$ are straight-chain alkyl and alkenyl radicals of no more than 6, preferably no more than 4, carbon atoms, eg. methyl, ethyl, isopropyl, tert.-butyl, n-propyl, isobutyl, neopentyl or allyl, cycloalkyl of 3 to 6 carbon atoms, eg. cyclopentyl, cyclopropyl or cyclohexyl, phenyl which is unsubstituted or substituted by methoxy, halogen, nitro, cyano or alkyl of 1 to 4 carbon atoms, or unsubstituted or substituted aralkyl, eg. 1-phenylethyl, 2-phenylethyl or benzyl which is unsubstituted or substituted by methoxy, halogen, nitro, cyano or alkyl of 1 to 4 carbon atoms.

Preferred compounds of the formula I are those in which $R^{14}$ is isopropyl, tert.-butyl or cyclopropyl and $R^{15}$ is alkyl of 1 to 4 carbon atoms, eg. methyl, ethyl, n-propyl, isopropyl, tert.-butyl, cyclopropyl or benzyl.

The acetylene compounds of the formula I can be obtained by a method wherein an appropriate ketone, for example the ketone II

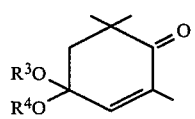
II is reacted with an acetylene compound III

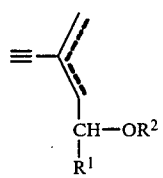
III in the presence of an inert solvent or diluent and in the presence of a base as the condensing agent.

Suitable basic condensing agents are alkali metal hydroxides, eg. KOH, alkali metal alcoholates, eg. $NaOCH_3$, $KOC_2H_5$ and K tert.-butylate, organo-alkali metal compounds, eg. n-butyl-lithium, organo-alkaline earth metal compounds. eg. $CH_3MgCl$ and $CH_3MgBr$, alkali metal hydrides, eg. KH and NaH, and alkali metal amides, eg. $NaNH_2$ and $KNH_2$. Preferred basic condensing agents are $CH_3MgCl$, KOH and potassium isobutylate.

Suitable inert solvents or diluents are ethers, eg. diethyl ether, diisopropyl ether, diethylene glycol dimethyl ether and tetrahydrofuran, aliphatic hydrocarbons, eg. benzene, toluene and xylene, amides, eg. dimethylformamide, N-methylpyrrolidone and hexamethylenephosphorotriamide, and amines, eg. ammonia.

The process may be carried out by adding the compound of the formula III to the suspension or solution of the condensing agent, introducing the ketone II, and then allowing the reaction to proceed to completion.

In some cases the reaction takes place at a very low temperature, but in general at from $-20°$ to $+65°$ C. Depending on the reactants, the condensing agent and the temperature, the reaction time can be from a few hours to several days. The reaction mixture is worked up in a conventional manner, for example by washing out the inorganic constituents, if necessary after the mixture has been neutralized with an acid.

Some of the ketones of the formula II which are required as starting compounds are known (U.S. Pat. No. 4,126,641); those which are unknown can be prepared by a conventional method from known intermediates, for example by monoketalization of 2,6,6-trimethylcyclohex-2-ene-1,4-dione (U.S. Pat. No. 4,076,854; Houben-Weyl, Methoden der Organischen Chemie, volume VI/3, pages 199 et seq., Georg Thieme Verlag, Stuttgart 1965).

The starting compounds of the formula II where $R^1$ is not hydrogen are known (Bull. Chem. Soc. Jap., 50 (1977) 1,584), and are readily obtainable from 3-methyl-pent-2-en-4-ynal by conventional acetalization methods (Bull. Chem. Soc. Jap., 49 (1976), 292).

Compounds of the formula III where $R^1$ is hydrogen are likewise known; these and the unknown compounds are obtainable from 3-methyl-pent-2-en-4-ynol by conventional etherification methods (J. Organomet. Chem., 117 (1976), 201).

Furthermore, all compounds of the formula III can also be prepared by dehydrating the corresponding carbinols of the formula

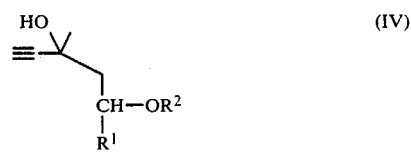

where $R^1$ and $R^2$ have the same meanings as in formula III, by a conventional method.

The carbinols of the formula IV in turn can be readily prepared in a conventional manner by ethinylating the corresponding methyl ketones (Houben-Weyl, Methoden der Organischen Chemie, volume IV/2, pages 413 et seq., Georg Thieme Verlag, Stuttgart, 1955).

Depending on the preparation process, the compounds of the formula III are obtained as a rule as a mixture of isomers, which can be isolated in a conventional manner, for example by chromatography. However, it is in general not necessary to separate the mixture of isomers before using the compound of the formula III to prepare the acetylene compound of the formula I.

The isomers of the formula III are referred to below as gem-III, corresponding to the formula

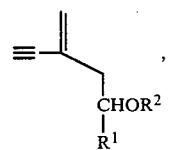

Z-III, corresponding to the formula

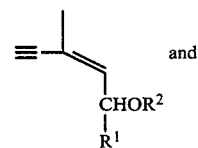
and

E-III, corresponding to the formula

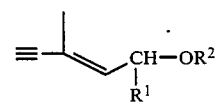

The acetalization of 3-metylpent-2-en-4-ynal and the etherification of 3-methylpent-2-en-4-ynol in general give Z-III/E-III mixtures, and no significant amounts of gem-III are formed. In contrast, relatively large amounts of geminally substituted ethylenes of the form gem-III are generally formed in addition when a compound of the formula V is dehydrated.

Depending on the type of substituents $R^1$ and $R^2$, each of the said isomers gem-III, Z-III and E-III can in turn consist of several isomers; this is the case, for example, when $R^1$ or $R^2$ contain chiral carbon atoms. These isomers mixtures can likewise be separated by a conventional method, but as a rule this is not necessary when the compounds are used to prepare the acetylene compounds of the formula I.

Accordingly, the acetylene compound of the formula I can likewise occur as a mixture of several isomers. In this mixture, the state of affairs in the side chain in respect of isomerism is in general related to the corresponding state of affairs in the compound of the formula III which is employed in each case as the starting compound, ie. depending on the relative amounts of the isomers gem-III, Z-III and E-III employed for the preparation, corresponding amounts of the corresponding isomers of the formulae gem-I, Z-I and E-I are obtained:

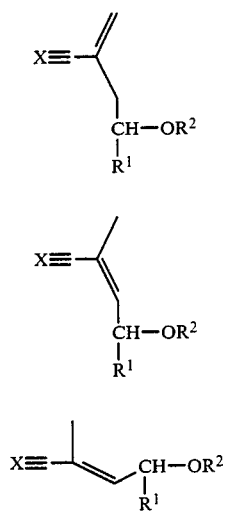

Depending on the type of substituents $R^1$, $R^2$, $R^3$, $R^4$, etc., each of the said isomers gem-I, Z-I and E-I may in turn consist of several isomers. Furthermore, the chirality of the carbon atom to which the hydroxyl groups are bonded forms the basis for the formation of further isomers of the compounds of the formula I. Mixtures of these isomers can be separated by a conventional, suitable method. Preferably, the acetylene compounds of the formula Z-I are employed as plant growth regulators, but separation of the isomer mixture is not usually required before it is used.

The Examples which follow illustrate the preparation of the acetylene compounds of the formula I, and of the intermediates of the formula III which are required for their preparation.

EXAMPLE 1

(a) Preparation of

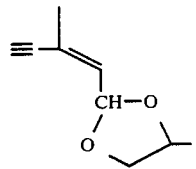

(1a)

153 g (2.0 moles) of propane-1,2-diol are added dropwise, in the course of two hours, to a boiling mixture of 150 g (1.6 moles) of 3-methylpent-2-en-4-ynal and 4.5 g of fumaric acid in 400 ml of n-hexane, while refluxing in a water separator. Thereafter, the mixture is heated for a further 5 hours until separation of water is complete, about 50 ml of a water/propanediol mixture being separated off by distillation. After the reaction mixture has cooled, an oil (about 150 ml, mainly propane-1,2-diol) is found to have been deposited at the bottom of the reaction flask; this oil is discarded. The supernatant hexane solution is separated off, washed with twice 150 ml of 5% strength aqueous sodium carbonate solution and then with twice 150 ml of water, and dried over sodium sulfate. Thereafter, the hexane is distilled off under reduced pressure and the residue which remains (126 g) is distilled under reduced pressure. After 6 g of first runnings at 51°–56° C./0.4 mbar, 107 g of the desired acetal 1a of boiling point 56° C./0.4 mbar are obtained. According to $^1$H-NMR and $^{13}$C-NMR, the product contains about 85% of the Z form and about 15% of the E form.

(b) Preparation of

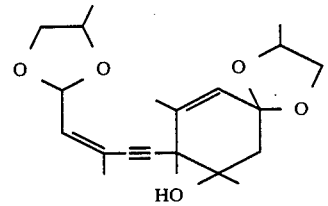

(1)

15.2 g of the acetal prepared in this manner are added dropwise, in the course of 30 minutes, to a stirred solution of 7.5 of methyl magnesium chloride in 67 ml of dry tetrahydrofuran at from 0° to 5° C., under a nitrogen atmosphere. The reaction mixture is left for 3 hours at 20° C., 17.5 g of the ketone of the formula

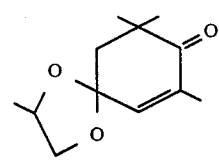

(1b)

are added dropwise in the course of 30 minutes while cooling at 0°–5° C., and the mixture is then stirred for 15 hours at 20° C. Hydrolysis is carried out by adding 20 ml of water dropwise while cooling with ice, the precipitate is filtered off and the filtrate is freed from tetrahydrofuran by distillation under reduced pressure. The residue is taken up in 200 ml of diethyl ether, the solution is washed with twice 100 ml of water, dried over sodium sulfate and filtered, and the ether is then distilled off under reduced pressure. The oil which remains (28 g) is then distilled in a bulb tube, unreacted starting material being distilled off at 50°–160° C./0.005 mbar. 19.4 g of the compound 1 remain. IR (film): 2,970, 2,920, 2,865, 1,445, 1,375, 1,345, 1,205, 1,150, 1,085, 1,045, 1,030, 980 and 960 cm⁻¹.

According to ¹H-NMR, the isomer mixture once again contains about 85% of the Z isomer and 15% of the E isomer.

EXAMPLE 2

(a) Preparation of

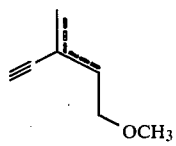
(2a)

A suspension of 50 g of anhydrous copper(II) sulfate in 250 ml of paraffin oil is heated at 160° C. while stirring, the pressure is brought to 135 mbar and thereafter 300 g of 3-hydroxy-3-methyl-5-methoxypentyne are slowly added dropwise to the suspension in the course of 4 hours. During this procedure, a mixture of water, starting material and dehydration product 2a is gradually collected in the vessel of an attached distillation bridge. After the addition is complete, the 180 g of distillate which has collected are taken up in 400 ml of diethyl ether, and the solution is washed with aqueous sodium bicarbonate solution and then with water, and dried over sodium sulfate. The ether is distilled off, 0.5 g of hydroquinone are added and the residue is then distilled fractionally under reduced pressure. 97 g of the compound 2a are obtained at 52°–60° C./67 mbar. According to the ¹H-NMR and ¹³C-NMR spectra, this product consists of the isomers gem-III, Z-III and E-III in the ratio of 60:30:10.

A further 58 g of a mixture of starting compound and compound 2a are collected as a higher boiling fraction at 61°–89° C./67 mbar, and this mixture may be used again in the dehydration.

(b) Preparation of

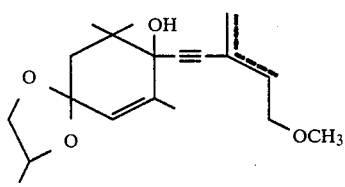
(2)

When the process described in Example 1(b) is used, with 7.5 g of methyl magnesium chloride, 11 g of the compound 2a and 17.5 g of 1b, and volatile constitutents are distilled off at 50°–180° C./0.001 mbar, the residue obtained is an oil which according to the ¹H-NMR spectrum contains various isomers 2 (60% of gem-2, 30% of Z-2 and 10% of E-2). IR (film): 2,970, 2,920, 2,870, 1,445, 1,380, 1,370, 1,345, 1,205, 1,090, 1,015, 980, 960 and 940 cm⁻¹.

Specific examples of acetylene compounds of the formula I are those given below.

EXAMPLE 3

Preparation of

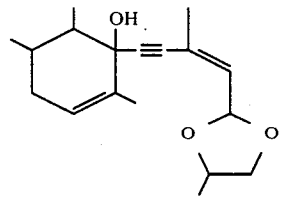
(3)

18.3 g of the acetal 1a are added dropwise, in the course of 30 minutes, to a stirred solution of 9 g of methyl magnesium chloride in 80 ml of dry tetrahydrofuran at from 0° to 5° C., under a nitrogen atmosphere. The reaction mixture is left for 3 hours at 20° C., 13.8 g of 2,5,6-trimethylcyclohex-2-en-1-one are added dropwise in the course of 30 minutes while cooling at 0°–5° C., and the mixture is then stirred for 15 hours at 20° C. Hydrolysis is carried out by adding 12 ml of water dropwise while cooling with ice, the precipitate is filtered off and the filtrate is freed from tetrahydrofuran by distillation under reduced pressure. The residue is taken up in 200 ml of diethyl ether, the solution is washed with twice 100 ml of water, dried over sodium sulfate and filtered, and the ether is then distilled off under reduced pressure. The oil which remains (28 g) is then distilled in a bulb tube, unreacted starting material being distilled off at 50°–160° C./0.005 mbar. Thereafter, 16.0 g of compound 3 distil over at 205°–210° C./0.005 mbar.

IR (film): 2,965, 2,925, 2,915, 2,875, 1,445, 1,375, 1,150, 1,080, 1,055, 1,045, 1,025 and 960 cm⁻¹.

According to ¹H-NMR spectra, the isomer mixture once again comprises about 85% of the Z isomer and 15% of the E isomer.

EXAMPLE 4

Preparation of (4)

When the process described in Example (3) is used, with 13.5 g of methyl magnesium chloride, 19.8 g of the compound 2a and 20.7 g of 2,6,6-trimethylcyclohex-2-en-1-one, and volatile constituents are distilled off at 50°–120° C./0.001 mbar, the second fraction obtained, at 125°–150° C. under the same pressure, is an oil (25 g), which according to the 1H-NMR spectrum consists of various isomers of the compound 4 (60% of gem-4, 30% of Z-4 and 10% of E-4). IR (film): 2,960, 2,940, 2,915, 2,870, 1,445, 1,375, 1,360, 1,115, 1,090, 1,075, 1,055, 1,030, 1,000, 975 and 965 cm⁻¹.

EXAMPLE 5

Preparation of

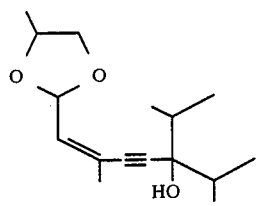

(5)

9.1 g of the acetal 1a are added dropwise, in the course of 30 minutes, to a stirred solution of 4.5 g of methyl magnesium chloride in 40 ml of dry tetrahydrofuran at from 0° to 5° C., under a nitrogen atmosphere. The reaction mixture is left for 3 hours at 20° C., 5.7 g of diisopropyl ketone are added dropwise in the course of 30 minutes while cooling at 0°–5° C., and the mixture is then stirred for 15 hours at 20° C. Hydrolysis is carried out by adding 6 ml of water dropwise while cooling with ice, the precipitate is filtered off and the filtrate is freed from tetrahydrofuran by distillation under reduced pressure. The residue is taken up in 200 ml of diethyl ether, the solution is washed with twice 100 ml of water, dried over sodium sulfate and filtered, and the ether is then distilled off under reduced pressure. The oil which remains (13 g) is then distilled in a bulb tube, unreacted starting material being distilled off at 50°–110° C./0.005 mbar. 10.8 g of the compound 5 remain. IR (film): 3,470, 2,970, 2,935, 2,875, 1,640, 1,445, 1,380, 1,320, 1,150, 1,055, 1,005, 980, 965, 955 and 935 cm$^{-1}$.

According to $^1$H-NMR, the isomer mixture once again contains about 85% of the Z isomer and 15% of the E isomer.

EXAMPLE 6

Preparation of

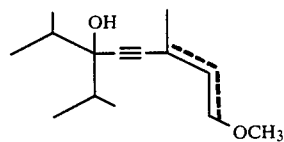

(6)

When the process described in Example (5) is used, with 5.0 of methyl magnesium chloride, 7.4 g of the compound 2a and 65 g of diisopropyl ketone, and volatile constituents are distilled off at 50°–80° C./0.001 mbar, the residue obtained is an oil (4.0 g), which according to the $^1$H-NMR spectrum contains various isomers 6 (60% of gem-6, 30% of Z-6 and 10% of E-6). IR (film): 3,450, 2,970, 1,470, 1,380, 1,150, 1,120, 1,105, 985, 955 and 905 cm$^{-1}$.

Further specific examples of acetylene compounds of the formula I are those given below:

| Compound no. | $R^1$ | $R^2$ | $R^3$ | $R^4$ | IR (film) cm$^{-1}$ | Comments (Ratio Z:E) |
|---|---|---|---|---|---|---|
| 7 | O—CH$_2$—C(CH$_3$)$_2$—CH$_2$— | | —CH$_2$—C(CH$_3$)$_2$—CH$_2$— | | 2945, 2870, 1630, 1465, 1390, 1360, 1195, 1095, 1020, 1010, 980, 960, 925 | 90% Z 10% E |
| 8 | —O—CH(CH$_3$)—CH$_2$— | | n-butyl | n-butyl | | |
| 9 | —O—CH(CH$_3$)—CH$_2$— | | n-hexyl | n-hexyl | | |
| 10 | n-butyl | n-butyl | —CH$_2$—CH(CH$_3$)— | | | |
| 11 | n-hexyl | n-hexyl | —CH$_2$—CH(CH$_3$)— | | | |
| 12 | n-hexyl | H | —CH$_2$—CH(CH$_3$)— | | | |

| Ex. no. | $R^2$ | $R^1$ | $R^6$ | $R^7$ | $R^8$ | $R^9$ | $R^{10}$ | $R^{11}$ | $R^{12}$ | $R^{13}$ | Endocyclic double bond | Isomer ratio gem:Z:E |
|---|---|---|---|---|---|---|---|---|---|---|---|---|
| 13 | CH$_3$ | —OCH$_3$ | CH$_3$ | CH$_3$ | H | H | H | H | H | CH$_3$ | yes | 0/90/10 |
| | IR (film): 2965, 2920, 2825, 1440, 1375, 1360, 1185, 1130, 1065, 1050, 1000, 950 cm$^{-1}$ | | | | | | | | | | | |
| 14 | —CH$_2$—C(CH$_3$)$_2$—CH$_2$—O— | | CH$_3$ | CH$_3$ | H | H | H | H | H | CH$_3$ | no | 0/90/10 |
| | IR (film): 2950, 2930, 2860, 2845, 1455, 1390, 1195, 1090, 1025, 1010, 980, 955, 925 cm$^{-1}$ | | | | | | | | | | | |
| 15 | —CH$_2$—CHCH$_3$—O— | | CH$_3$ | CH$_3$ | H | H | H | H | H | CH$_3$ | no | 0/85/15 |
| | IR (film): 2955, 2920, 2865, 2850, 1455, 1440, 1370, 1310, 1145, 1035, 955, 935 cm$^{-1}$ | | | | | | | | | | | |
| 16 | —CH$_2$—CHCH$_3$—O— | | CH$_3$ | H | CH$_3$ | H | H | H | H | H | no | 0/85/15 |
| | IR (film): 2965, 2920, 2870, 1450, 1375, 1145, 1055, 1050, 1030, 1005, 990, 960, 935 cm$^{-1}$ | | | | | | | | | | | |
| 17 | —CH$_2$—CH$_2$—O— | | CH$_3$ | CH$_3$ | H | H | H | H | H | CH$_3$ | no | 0/80/20 |
| | IR (film): 2960, 2930, 2880, 1455, 1445, 1375, 1355, 1335, 1325, 1145, 1125, 1060, 1030, 950 cm$^{-1}$ | | | | | | | | | | | |
| 18 | —CH$_2$—CHCH$_3$—O— | | H | H | CH$_3$ | CH$_3$ | H | H | CH$_3$ | H | yes | 0/85/15 |
| | IR (film): 2945, 2920, 2885, 2860, 1445, 1370, 1360, 1145, 1070, 1040, 1010, 990, 960, 930 cm$^{-1}$ | | | | | | | | | | | |
| 19 | —CH$_2$—CHCH$_3$—O— | | H | H | —C(=CH$_2$)CH$_3$ | | H | H | H | CH$_3$ | yes | 0/85/15 |
| | IR (film): 2970, 2920, 2880, 1450, 1375, 1150, 1035, 955, 890 cm$^{-1}$ | | | | | | | | | | | |
| 20 | —CH$_2$—CHCH$_3$—O— | | H | H | H | H | H | H | H | H | yes | 0/85/15 |
| | IR (film): 2965, 2920, 1435, 1370, 1310, 1195, 1140, 1040, 950, 925 cm$^{-1}$ | | | | | | | | | | | |
| 21 | —CH$_2$—CHCH$_3$—O— | | H | H | H | H | CH$_3$ | CH$_3$ | H | CH$_3$ | yes | 0/85/15 |
| | IR (film): 2950, 2860, 1440, 1370, 1350, 1305, 1140, 1040, 1015, 1000, 955, 925 cm$^{-1}$ | | | | | | | | | | | |
| 22 | —CH$_2$CHCH$_3$—O— | | —CH(CH$_3$)$_2$ | H | H | H | H | H | H | H | no | 0/85/15 |
| | IR (film): 2930, 2865, 1435, 1370, 1355, 1310, 1140, 1115, 1085, 1040, 995, 960, 930 cm$^{-1}$ | | | | | | | | | | | |
| 23 | —CH$_2$—CHCH$_3$—O— | | —C(CH$_3$)$_2$ | H | H | H | H | H | H | H | no | 0/85/15 |
| | IR (film): 2930, 2865, 1435, 1385, 1370, 1355, 1135, 1075, 1040, 960, 935 cm$^{-1}$ | | | | | | | | | | | |
| 24 | —CH$_2$CHCH$_3$—O— | | H | H | H | H | H | H | H | H | no | 0/85/15 |
| | IR (film): 2965, 2930, 2850, 1435, 1365, 1330, 1320, 1305, 1140, 1120, 1045, 990, 955, 930 cm$^{-1}$ | | | | | | | | | | | |
| 25 | —CH$_2$—CHCH$_3$—O— | | H | CH$_3$ | H | H | H | H | H | CH$_3$ | yes | 0/85/15 |
| | IR (film): 2980, 2935, 2890, 1455, 1385, 1330, 1155, 1050, 1010, 970 cm$^{-1}$ | | | | | | | | | | | |
| 26 | CH$_3$ | H | H | H | H | H | H | H | H | H | yes | 60/30/10 |
| | IR (film): 3414, 2932, 2866, 2838, 1376, 1358, 1108, 1060, 960 cm$^{-1}$ | | | | | | | | | | | |

-continued

| Ex. no. | | | | | | | | | | | | |
|---|---|---|---|---|---|---|---|---|---|---|---|---|
| 27 | CH₃ | H | CH₃ | CH₃ | CH₃ | H | H | H | H | CH₃ | yes | 60/30/10 |
| | IR (film): 3455, 2974, 2957, 2881, 1453, 1387, 1376, 1102, 1061, 1014 cm⁻¹ | | | | | | | | | | | |
| 28 | CH₃ | H | CH₃ | CH₃ | H | H | H | H | H | CH₃ | yes | 60/30/10 |
| | IR (film): 3433, 2973, 2929, 2875, 1452, 1376, 1110, 1076, 1054, 1004 cm⁻¹ | | | | | | | | | | | |
| 29 | CH₃ | H | CH₃ | CH₃ | H | H | H | H | H | CH₃ | yes | 60/30/10 |
| | IR (film): 2960, 2920, 1440, 1370, 1350, 1110, 1070, 1050, 1035, 995, 975, 960 cm⁻¹ | | | | | | | | | | | |
| 30 | CH₃ | H | CH₃ | CH₃ | H | CH₃ | H | H | H | CH₃ | yes | 60/30/10 |
| | IR (film): 2980, 2960, 2930, 2890, 2835, 1455, 1385, 1120, 1015, 1005, 915, 905 cm⁻¹ | | | | | | | | | | | |
| 31 | CH₃ | H | CH₃ | CH₃ | H | H | H | H | H | CH₃ | no | 60/30/10 |
| | IR (film): 2950, 2920, 2860, 1450, 1370, 1110, 1070, 1050, 1025, 965, 945 cm⁻¹ | | | | | | | | | | | |
| 32 | n-C₆H₁₃ | H | CH₃ | CH₃ | H | H | H | H | H | CH₃ | yes | |
| 33 | n-C₄H₉ | H | CH₃ | CH₃ | H | H | H | H | H | CH₃ | yes | |
| 34 | n-C₄H₉ | n-C₄H₉O | CH₃ | CH₃ | H | H | H | H | H | CH₃ | yes | |
| 35 | n-C₆H₁₃ | n-C₆H₁₃O | CH₃ | CH₃ | H | H | H | H | H | CH₃ | yes | |

| Ex. no. | R² R¹ | R¹⁴ | R¹⁵ | IR (film) [cm⁻¹] | Isomer ratio gem:Z:E |
|---|---|---|---|---|---|
| 36 | —CH₂—C(CH₃)₂—CH₂—O— | isopropyl | isopropyl | 2955, 2865, 2840, 1465, 1390, 1140, 1090, 1010, 980, 960, 950, 925 | 0/90/10 |
| 37 | —CH₂—C(CH₃)₂—CH₂—O— | cyclopropyl | cyclopropyl | 3000, 2950, 2845, 1465, 1445, 1390, 1360, 1305, 1230, 1140, 1085, 1020, 975, 960, 925 | 0/90/10 |
| 38 | —CH₂—CH(CH₃)—O— | phenyl | cyclopropyl | 3440, 2980, 2960, 2930, 2885, 1445, 1375, 1150, 1085, 1040, 1005, 965, 925, 755, 705 | 0/85/15 |
| 39 | —CH₂—CH(CH₃)—O— | cyclopropyl | cyclopropyl | 3450, 3005, 2975, 2930, 2875, 1440, 1375, 1315, 1145, 1050, 1030, 995, 960, 930 | 0/85/15 |
| 40 | —CH₂—CH(CH₃)—O— | isopropyl | phenyl | 2965, 2920, 2870, 1440, 1370, 1145, 1055, 1030, 1000, 955, 935, 755, 700 | 0/85/15 |
| 41 | —CH₂—CH(CH₃)—O— | cyclopropyl | 4-methoxy-phenyl | 2975, 1605, 1505, 1375, 1295, 1245, 1170, 1145, 1030, 990, 965, 830 | 0/85/15 |
| 42 | —CH₂—CH(CH₃)—O— | cyclopentyl | phenyl | 2950, 2865, 1440, 1370, 1145, 1030, 995, 960, 930, 700 | 0/85/15 |
| 43 | —CH₂—CH(CH₃)—O— | t-butyl | methyl | 3450, 2960, 2920, 2865, 1445, 1370, 1315, 1190, 1140, 1080, 1050, 1005, 960, 935, 905 | 0/85/15 |
| 44 | —CH₂—CH(CH₃)—O— | ethyl | t-butyl | 3460, 2960, 2920, 2865, 1440, 1385, 1370, 1355, 1135, 1100, 1045, 990, 955 | 0/85/15 |
| 45 | —CH₂—CH(CH₃)—O— | isobutyl | isobutyl | 3450, 2945, 2920, 2860, 1460, 1440, 1375, 1360, 1145, 1050, 1005, 960, 930 | 0/85/15 |
| 46 | —CH₂—CH(CH₃)—O— | methyl | neopentyl | 3450, 2970, 2945, 2895, 2865, 1460, 1445, 1390, 1375, 1360, 1145, 1105, 1075, 1050, 1015, 995, 960, 930 | 0/85/15 |
| 47 | —CH₂—CH(CH₃)—O— | propen-2-yl | propen-2-yl | 2975, 2925, 2875, 1635, 1440, 1370, 1145, 1125, 1050, 990, 960, 935, 905 | 0/85/15 |
| 48 | —CH₂—CH(CH₃)—O— | 1-propyl | ethyl | 3450, 2970, 2940, 2885, 1450, 1375, 1325, 1145, 1055, 1000, 960 | 0/85/15 |
| 49 | —CH₂—CH(CH₃)—O— | isobutyl | methyl | 3450, 2970, 2950, 2920, 2865, 1440, 1375, 1360, 1145, 1080, 1050, 995, 960, 930 | 0/85/15 |
| 50 | —CH₂—CH(CH₃)—O— | 1-propyl | 1-propyl | 3450, 2955, 2925, 2865, 1440, 1370, 1135, 1070, 1050, 990, 975, 955, 930 | 0/85/15 |
| 51 | —CH₂—CH(CH₃)—O— | 2-phenyl-ethyl-(2) | isopropyl | 2960, 2920, 2870, 1445, 1375, 1140, 1050, 1020, 995, 980, 960, 760, 700 | 0/85/15 |

The acetylene compounds of the formula I influence plant metabolism, and may therefore be used as plant growth regulators.

Experience has shown that plant growth regulators may have either one or several different effects on plants.

The diversity of action of growth regulators depends especially on (a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation of the active ingredient; and
(g) the concentration at which the active ingredient is applied.

At all events, plant growth regulators have a positive and desired effect on crop plants.

A description of some of the various possibilities of using the growth regulators according to the invention in agriculture and horticulture is given below.

A. Transpiration in crop plants may be influenced by the compounds according to the invention. Treatment with these compounds results in an increased closure of the stomata and thus in considerably decreased transpiration. As a result, the treated plants are much more resistant to water-shortage stress than untreated ones. It is thus possible to avoid damage to crop plants caused by this stress factor (which can lead to yield losses or complete withering of the plants), and to regulate the water regime.

B. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to ledge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

A further mechanism for increasing yields with growth regulators is based on the fact that the nutrients are employed to a greater extent for blossom and fruit formation, whereas vegetative growth is restricted. Because the leaf or plant mass is relatively low, this also counteracts attack by various, particularly fungal, diseases.

The inhibition of vegetative growth also makes closer planting possible in numerous crops, which means an increase in yield based on the area cropped. The compounds according to the invention are particularly suitable for suppressing vegetative growth in crops plants such as soybeans, sunflowers, groundnuts, rape, ornamentals, cotton, rice and grasses.

C. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

D. Finally, it is also possible with growth regulators to shorten or lengthen growth stages and to accelerate or retard the ripening process in plant parts either before or after harvesting. In particular, senescence may be accelerated with the compounds according to the invention.

A factor of economical interest is for example the facilitation of harvesting made possible by a temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of plants. This mode of action is particularly pronounced with the compounds according to the invention.

The action of the acetylene compounds is superior to that of prior art growth regulators. This action is manifested not only in monocotyledon crops, e.g., cereals such as wheat barley, rye, oats and rice or Indian corn or grasses, but also in dicotyledons (e.g., sunflowers, tomatoes, groundnuts, grapes, cotton, rape, sugarbeets and soybeans) and varous ornamentals such as chrysanthemums, poinsettias and hibiscus.

The compounds according to the invention may be applied to the crop either by treating the seed, treating the soil, i.e., through the roots, or—the method particularly preferred—by spraying the leaves.

Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.001 to 12 kg/ha, preferably from 0.01 to 3 kg/ha, are generally considered to be sufficient.

The agents according to the invention can be applied in conventional formulations, e.g., solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine, ketones, e.g. cyclohexanone, dimethylformamide, and water; solid carriers, for example natural rock powders, e.g. kaolin, alumina, talc and chalk, and synthetic rock powders, e.g. highly disperse silica and silicates; emulsifiers, and other surfactants, for example non-ionic and anionic emulsifiers, e.g. polyoxyethylene fatty alcohol ethers and alkylsulfonates, and dispersants, for example lignin, sulfite waste liquors and methylcellulose. The formulations in general contain from 0.1 to 95% by weight of active ingredient, preferably from 0.5 to 90%.

The formulations, and the ready-to-use preparations obtained therefrom, e.g. solutions, emulsions, suspensions, powders, dusts, pastes or granules, are applied in the conventional manner, e.g., preemergence, postemergence, or as seed disinfectants.

Examples of formulations are given below.

I. 20 parts by weight of the compound of Example 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and titrurated in a hammer mill. By uniformly distributing the mixture in 20,000 parts by weight of water, a spray liquor is obtained containing 0.1% by weight of the active ingredient.

II. 3 parts by weight of the compound of Example 1 is intimately mixed with 97 parts by weight of particulate kaolin. A dust is obtained containing 3% by weight of the active ingredient.

III. 30 parts by weight of the compound of Example 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 3 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt.% of active ingredient.

V. 20 parts of the compound of Example 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 partes of a paraffinic mineral oil. A stable oily dispersion is obtained.

VI. 90 parts by weight of the compound of Example 1 is mixed with 10 parts by weight of N-methyl-alpha-pyrrolidone. A mixture is obtained which is suitable for application in the form of very fine drops.

VII. 20 parts by weight of the compound of Example 1 is dissolved in a mixture consisting of 80 parts by weight of xylene, 10 parts by weight of the adduct of 8 to 10 moles of ethylene oxide and 1 mole of oleic acid-N-monomethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

The agents according to the invention may in these application forms, also be mixed and applied with other active ingredients, e.g., herbicides, insecticides, other growth regulators, fungicides and fertilizers. When mixed with other growth regulators, the spectrum of action is in many cases increased; with a number of these compositons, synergistic effects also occur; i.e., the action of the combination product is greater than the effect of the individual components added together.

Examples of fungicides which may be combined with the compounds according to the invention are: dithiocarbamates and their derivatives, e.g. iron(III) dimethyldithiocarbamate, zinc dimethyldithiocarbamate, manganese, N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N;-polyethylene-bis-(thiocarbamoyl)-disulfide, zinc N,N;-propylene-bis-dithiocarbamate, and the ammonia complex of zinc N,N;-propylene-bis-dithiocarbamate and N,N;-polypropylene-bis-(thiocarbamoyl)-disulfide; nitro derivatives, e.g. dinitro-(1-methylheptyl)-phenyl cortonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenyl-hydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, D,L-methyl-N-(2,6-dimethylphenyl)-N-fur-2-yl-alanate, methyl D,L-N-(2,6-dimethylphenyl)-N-(2'-methoxyacetyl)-alanate, diisopropyl 5-nitroisophthalate, 2,5-dimethyl-furan-3-carboxylic acid anilide, 2,5-dimethylfuran-3-carboxylic acid cyclohexylamide, 2-methyl-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, 2,3-dichloro-1,4-naphthoquinone, 1,4-dichloro-2,5-dimethoxybenzene, p-dimethylaminobenzene diazine sodium sulfonate, 1-chloro-2-nitropropane, polychloronitrobenzenes, such as pentachloronitrobenzene, methyl isocyanate, fungicidal antibiotics, such as grisofulvin and kasugamycin, tetrafluorodichloroacetone, 1-phenylthiosemicarbazide, Bordeaux mixture, nickel-containing compounds, and sulfur.

The following example demonstrate the action of the acetylene compounds of the formula I to be used in accordance with the invention as growth regulators; however, further applications as growth regulators are not excluded.

The transpiration-inhibiting action of the acetylene compounds of the formula I may be illustrated for example by assessing wilt after water-shortage stress, by determining water consumption, and by measuring the resistance to diffusion.

1. Wilt after water-shortage stress (greenhouse experiment)

Plants, e.g., barley, were grown conventionally, in plastic pots approx. 12.5 cm in diameter, in a peat substrate provided with sufficient nutrients. The substrate was completely saturated with water until the leaves were sprayed. The application rates were 0.2 and 0.1 mg of active ingredient per pot. After the aqueous active ingredient formulations had been applied, the pots were kept in dry pallets without any further addition of water. Plant wilt was assessed on the following scale: 0=no wilt, 9=total wilt.

In this test, active ingredient nos. 1, 2, 3, 4, 5, 7 to 33, 40, 43, 47, 50, 55, 56, 57, 58 and 59 had a good transpiration-inhibiting action.

2. Water consumption (short-term experiment in the lab.)

Young sunflowers grown as in the above experiment were sprayed, when approx. 25 cm high, with aqueous formulations of the candidate compounds. Immediately after spraying the plants were cut approx. 10 cm below the vegetation center and placed in graduated centrifuge tubes. The application rates were 0.2 and 0.1 mg of active ingredient per pot. The tubes were kept at room temperature, in diffuse light and free from draughts, and the water consumption was determined by means of the graduations. At the end of the experiment (after 24 hours) the leaf surface area of the flowers employed in the experiment was measured with a leaf surface area measuring device from LJ-COR Inc. and expressed as μl/cm².

In this test, the water consumption of plants treated with active ingredients nos. 1, 2, 3 and 7 was much lower than that of untreated plants.

3. Resistance to diffusion (greenhouse experiment)

Test plants (sunflowers, soybeans) were grown as described above, sprayed with aqueous formulations of the compounds, and kept in the greenhouse with a normal water supply. The application rates were 0.2 and 0.1 mg of active ingredient per pot. The diffusion resistance of the leaves—as a parameter for the degree of opening of the stomata—was determined by means of an autoporometer.

This test revealed that the diffusion resistance of the leaves of the plants treated with active ingredients 1, 2, 3 and 7 was greater than that of the leaves of untreated plants.

4. Growth-regulating properties

To determine the growth-regulating properties of the acetylene compounds of the formula I, test plants were grown in a substrate provided with sufficient nutrients in plastic vessels about 12.5 cm in diameter.

In the preemergence method, the candidate compounds were poured as aqueous formulations on to the seedbed on the day of sowing.

In the postemergence method, the candidate compounds were sprayed on to the plants as aqueous formulations. The growth-regulating action observed was confirmed at the end of the experiment by height measurements. The values obtained were compared with those for untreated plants.

Not only was growth height reduced—the leaves also took on a more intense color. The increased chlorophyll content is indicative of a higher rate of photosynthesis, making for bigger yields.

In this test, active ingredients nos. 1, 2, 3, 4, 15, 17, 19, 24, 25, 27, 29, 30, 31, 32, 33, 47, 48, 50, 51, 52, 53, 54, 56, 57, 59 and 60 had, both on preemergence and postemergence application, a pronounced growth-regulating action.

We claim:

1. A acetylene compound of the formula

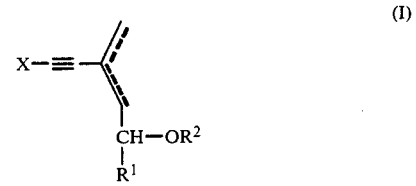

where one of the ---- lines is a double bond and the other is a single bond, $R^1$ is $-OR^5$, and $R^5$, together with $R^2$, forms a methylene chain of the formula $-(CH_2)_n-$ where n is 2, 3 or 4, and can be monosubstituted or disubstituted by alkyl of 1 to 4 carbon atoms, and X is one of the radicals

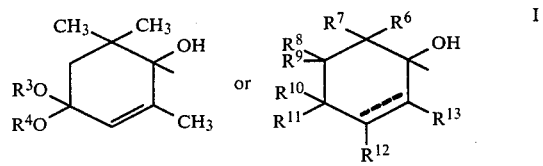

where $R^3$ and $R^4$ are identical and are each alkyl of 1 to 6 carbon atoms, or together form a methylene chain which is of the formula $-(CH_2)_n-$ where n is 2, 3 or 4, and can be monosubstituted or disubstituted by alkyl of 1 to 4 carbon atoms, and $R^6$ is hydrogen, methyl, ethyl, isopropyl or tert.-butyl, $R^8$ is hydrogen, straight-chain or branched alkyl or alkenyl of no more than 4 carbon atoms, and $R^7$, $R^9$, $R^{10}$, $R^{11}$, $R^{12}$ and $R^{13}$ are each hydrogen or methyl, and substituents $R^6$ to $R^{13}$ being in any stereochemical arrangement relative to each other and relative to the acetylenic side-chain and the endocyclic ---- line denotes a double or single bond.

2. An acetylene compound of the formula I as defined in claim 1, wherein n is 2.

3. A process for regulating plant growth which comprises applying to the plants or the seed thereof a plant growth regulating effective amount of a composition containing an effective amount of the compound of claim 1.

4. A process for reducing transpiration in plants which comprises applying to plants or their seed, a transpiration reducing effective amount of a composition comprising solvents and/or carriers and an effective amount of an acetylenic compound of the formula

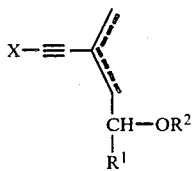

(I)

where one of the ---- lines is the double bond and the other is a single bond, $R^1$ is $—OR^2$ and $R^2$ is alkyl of 1 to 6 carbon atoms, or $R^1$ is $—OR^5$, and $R^5$, together with $R^2$, forms a methylene chain of the formula $—(CH_2)_n—$ where n is 2, 3, or 4, and can be monosubstituted or disubstituted by alkyl of 1 to 4 carbon atoms, and X is one of the radicals

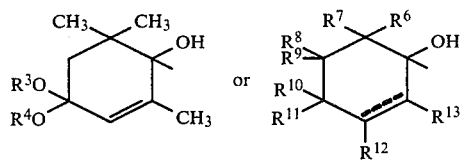

where $R^3$ and $R^4$ are identical and are each alkyl of 1 to 6 carbon atoms, or together form a methylene chain which is of the formula $—(CH_2)_n—$ where n is 2, 3 or 4, and can be monosubstituted or disubstituted by alkyl of 1 to 4 carbon atoms, and $R^6$ is hydrogen, methyl, ethyl, isopropyl or tert.-butyl, $R^8$ is hydrogen, straight-chain or branched alkyl or alkenyl of no more than 4 carbon atoms, and $R^7$, $R^9$, $R^{10}$, $R^{11}$, $R^{12}$ and $R^{13}$ are each hydrogen or methyl, and substituents $R^6$ to $R^{13}$ being in any sterochemical arrangement relative to each other and relative to the acetylenic side-chain and the endocyclic ---- line denotes a double bond or a single bond.

5. A process for regulating platn growth which comprises applying to the plants or the seed thereof a plant growth regulating effective amount of the composition of claim 3 wherein n is 2.

6. A process for reducing transpiration in plants which comprises applying to plants or their seed a transpiration reducing effective amount of the composition of claim 4 wherein $R^1$ is $OR^2$ and $R^2$ is alkyl of 1 to 4 carbon atoms.

7. A process for reducing transpiration in plants which comprises applying to plants or their seed a transpiration reducing effective amount of the composition of claim 4 wherein $R^1$ is $OR^5$ and n is 2.

* * * * *

UNITED STATES PATENT AND TRADEMARK OFFICE
CERTIFICATE OF CORRECTION

PATENT NO. : 4,671,816

DATED : June 9, 1987

INVENTOR(S) : Jens-Uwe BLIESNER et al.

It is certified that error appears in the above-identified patent and that said Letters Patent is hereby corrected as shown below:

On the title page

Please add:

(30) Foreign Application Priority Data:

November 4, 1981 (DE) Fed. Rep. of Germany...3143720

November 4, 1981 (DE) Fed. Rep. of Germany...3143721

November 4, 1981 (DE) Fed. Rep. of Germany...3143722

Signed and Sealed this

Second Day of August, 1988

*Attest:*

DONALD J. QUIGG

*Attesting Officer*     *Commissioner of Patents and Trademarks*